(12) United States Patent
Miyazaki et al.

(10) Patent No.: US 11,313,932 B2
(45) Date of Patent: Apr. 26, 2022

(54) MAGNETIC RESONANCE IMAGING APPARATUS AND MAGNETIC RESONANCE IMAGING METHOD

(71) Applicant: CANON MEDICAL SYSTEMS CORPORATION, Otawara (JP)

(72) Inventors: Mitsue Miyazaki, Vernon Hills, IL (US); Yoshimori Kassai, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 128 days.

(21) Appl. No.: 16/790,792

(22) Filed: Feb. 14, 2020

(65) Prior Publication Data

US 2021/0255265 A1 Aug. 19, 2021

(51) Int. Cl.
*G01R 33/54* (2006.01)
*A61B 5/055* (2006.01)
*G01R 33/48* (2006.01)

(52) U.S. Cl.
CPC ............ *G01R 33/543* (2013.01); *A61B 5/055* (2013.01); *G01R 33/4814* (2013.01); *G01R 33/4824* (2013.01)

(58) Field of Classification Search
USPC ........................................................ 324/309
See application file for complete search history.

(56) References Cited

U.S. PATENT DOCUMENTS

| 2004/0061496 | A1* | 4/2004 | Ookawa ............... G01R 33/563 324/307 |
| 2009/0309592 | A1 | 12/2009 | Furudate |
| 2017/0108568 | A1* | 4/2017 | Sueoka ............ G01R 33/4833 |
| 2017/0219672 | A1 | 8/2017 | Miyazaki et al. |
| 2017/0307765 | A1 | 10/2017 | Mugler, III et al. |

FOREIGN PATENT DOCUMENTS

JP 2014-36901 A 2/2014

OTHER PUBLICATIONS

Ohno, Y. et al. "Pulmonary High-Resolution Ultrashort TE MR Imaging: Comparison with Thin-Section Standard-and Low-Dose Computed Tomography for the Assessment of Pulmonary Parenchyma Diseases", JMRI, 2016, pp. 512-532.

(Continued)

*Primary Examiner* — Rodney E Fuller
(74) *Attorney, Agent, or Firm* — Oblon, McClelland, Maier & Neustadt, L.L.P.

(57) ABSTRACT

A magnetic resonance imaging apparatus according to an embodiment includes sequence controlling circuitry and processing circuitry. The sequence controlling circuit executes, while a k-space is divided into a plurality of segments, a pulse sequence by which a tag pulse is applied and subsequently acquisition is performed. The processing circuit generates an image based on the pulse sequence executed by the sequence controlling circuit. The pulse sequence is a pulse sequence by which the acquisition is repeatedly performed at the center of the k-space. The sequence controlling circuit executes the pulse sequence, while changing the range to which the tag pulse is applied, for each of the plurality of segments.

8 Claims, 12 Drawing Sheets

(56) References Cited

OTHER PUBLICATIONS

Extended European Search Report dated Jul. 7, 2021 in European Patent Application No. 21156946.2, 9 pages.
Albert, T., M.D., et al., "Time-Spatial Labeling Inversion Pulse—Safe, Simple and Effective Non-Contrast MR Angiography", Jan. 1, 2002, XP055818512, Retrieved from the Internet: URL: https://us.medical.canon/download/mr-wp-titan-15t-time-spatial [retrieved on Jun. 28, 2021], p. 2121, 7 total pages.
Middlebrooks, E.H, et al., "Relation between tag position and degree of visualized cerebrospinal fluid reflux into the lateral ventricles in time-spatial labeling inversion pulse magnetic resonance imaging at the foramen of Monro", Fluids and Barriers of the CNS, vol. 12, No. 1, XP055818497, Jun. 2015, pp. 1-5.

\* cited by examiner

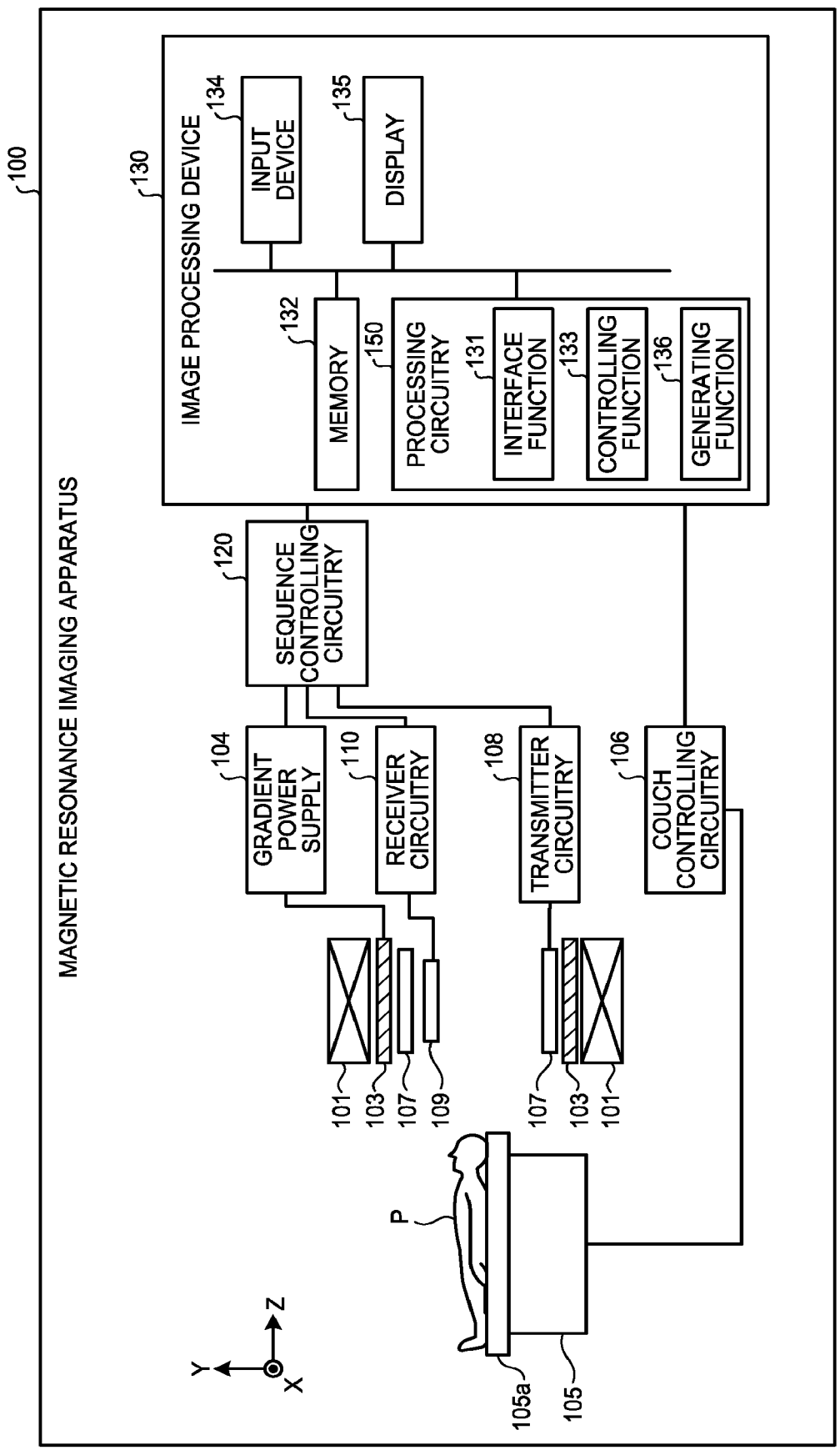

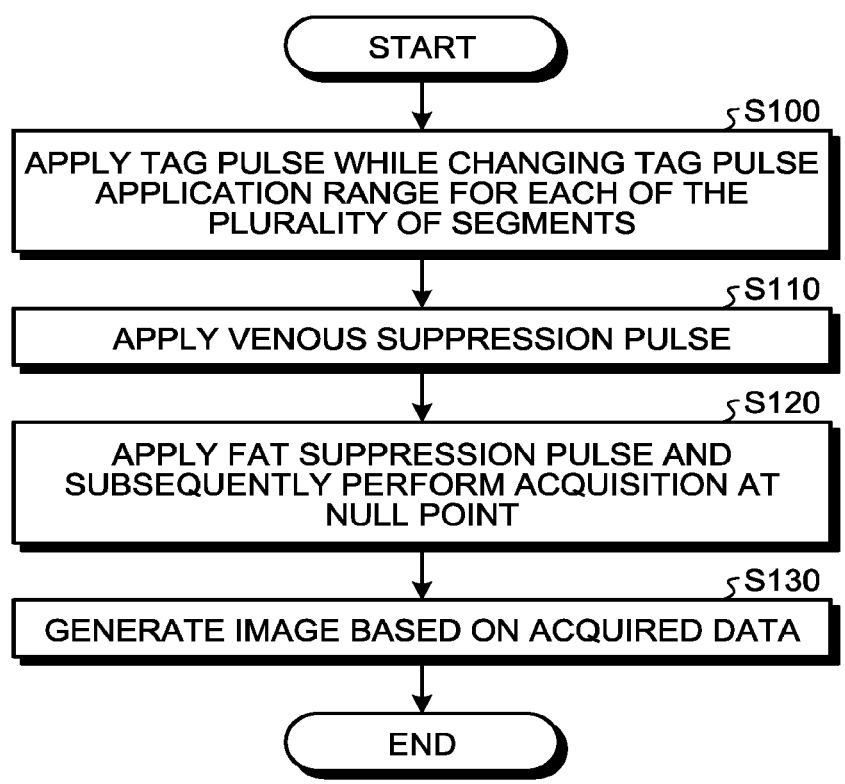

DIRECTION OF VENOUS BLOOD FLOW

DIRECTION OF ARTERIAL BLOOD FLOW

DIRECTION OF VENOUS BLOOD FLOW

MAGNETIC RESONANCE IMAGING APPARATUS AND MAGNETIC RESONANCE IMAGING METHOD

FIELD

Embodiments described herein relate generally to a magnetic resonance imaging apparatus and a magnetic resonance imaging method.

BACKGROUND

In magnetic resonance imaging, there is a method called three-dimensional ultrashort echo time (3D UTE) imaging method. The 3D UTE imaging method has the following characteristics: signals have high sensitivity because the echo time (TE) is short; resistance to motion artifact is relatively high because oversampling is performed at the center of a k-space; and the imaging is not easily affected by susceptibility.

To selectively capture an image of a blood vessel, it is desirable to suppress background signals (and fat signals). Accordingly, it is possible to render the aorta, the abdominal aorta, peripheral sites, or the like in images, by applying a tag pulse while using a Time-Spatial Labeling Inversion Pulse (Time-SLIP) method and combining 3D UTE acquisition with a flow-in method of the Time-SLIP scheme. By combining the 3D UTE imaging with the Time-SLIP method in this manner, it is possible to acquire three-dimensional k-space data, while suppressing the background signals.

For blood vessels having a relatively high flow rate, it is possible to render blood in images by combining the 3D UTE acquisition with the Time-SLIP method; however, to render a blood vessel having a relatively low flow rate like in the situations where Non-Contrast Magnetic Resonance Angiography (NC-MRA) is implemented on a peripheral site, it is difficult to render the blood vessel in images by simply combining the 3D UTE acquisition with the Time-SLIP method.

BRIEF DESCRIPTION OF THE DRAWINGS

FIG. 1 is a diagram illustrating a magnetic resonance imaging apparatus according to an embodiment;

FIG. 4 is a flowchart for explaining a process performed by a magnetic resonance imaging apparatus according to a first embodiment;

DETAILED DESCRIPTION

Figure 2A:
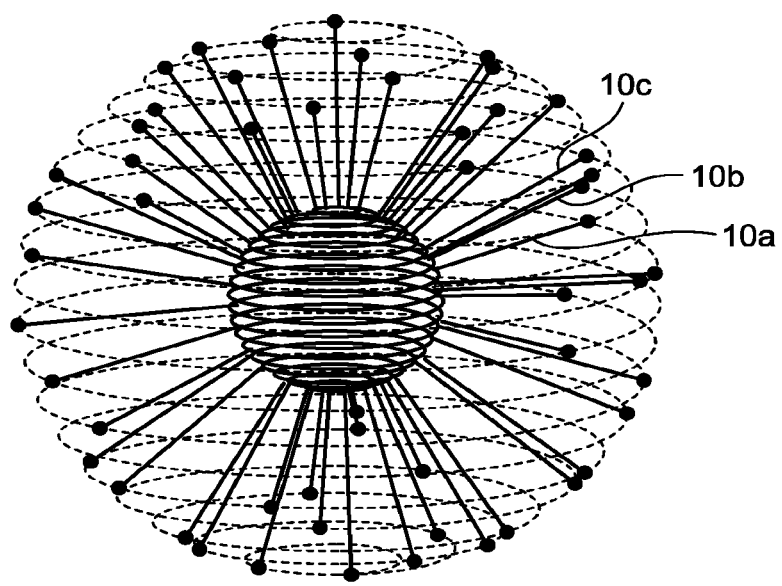
FIGS. 2A, 2B, and 2C are drawings illustrating examples of acquisition processes performed by the magnetic resonance imaging apparatus according to the embodiment.

A magnetic resonance imaging apparatus according to an embodiment includes sequence controlling circuitry and processing circuitry. The sequence controlling circuitry executes, while a k-space is divided into a plurality of segments, a pulse sequence by which a tag pulse is applied and subsequently acquisition is performed. The processing circuitry generates an image based on the pulse sequence executed by the sequence controlling circuitry. The pulse sequence is a pulse sequence by which the acquisition is repeatedly performed at the center of the k-space. The sequence controlling circuitry executes the pulse sequence, while changing a range to which the tag pulse is applied, for each of the plurality of segments.

Exemplary embodiments of the present disclosure will be explained, with reference to the accompanying drawings. Some of the constituent elements that are the same as each other will be referred to by using the same reference characters, and the duplicate explanations thereof will be omitted.

First Embodiment

FIG. 1 is a block diagram illustrating a magnetic resonance imaging apparatus 100 according to a first embodiment. As illustrated in FIG. 1, the magnetic resonance imaging apparatus 100 includes a static magnetic field magnet 101, a static magnetic field power supply (not illustrated), a gradient coil 103, a gradient power supply 104, a couch 105, couch controlling circuitry 106, a transmitter coil 107, transmitter circuitry 108, a receiver coil 109, receiver circuitry 110, and sequence controlling circuitry 120 (a sequence controlling unit), and an image processing device 130. The magnetic resonance imaging apparatus 100 does not include an examined subject (hereinafter "patient") P (e.g., a human body). The configuration illustrated in FIG. 1 is merely an example. For instance, any of the functional units in the sequence controlling circuitry 120 and the image processing device 130 may be integrated together or configured separately as appropriate.

The static magnetic field magnet 101 is a magnet formed to have a hollow and substantially circular cylindrical shape and is configured to generate a static magnetic field in the space inside thereof. For example, the static magnetic field magnet 101 is a superconductive magnet or the like and gets magnetically excited by receiving supply of an electric current from the static magnetic field power supply. The static magnetic power supply is configured to supply the electric current to the static magnetic field magnet 101. Alternatively, the static magnetic field magnet 101 may be a permanent magnet. In that situation, the magnetic resonance imaging apparatus 100 does not have to be provided with a static magnetic field power supply. Further, the static magnetic field power supply may be provided separately from the magnetic resonance imaging apparatus 100.

The gradient coil 103 is a coil formed to have a hollow and substantially circular cylindrical shape and is arranged on the inside of the static magnetic field magnet 101. The gradient coil 103 is formed by combining together three coils corresponding to X-, Y-, and Z-axes that are orthogonal to one another. The three coils are configured to individually receive supply of an electric current from the gradient power supply 104 and to generate gradient magnetic fields of which the magnetic field intensities vary along the X-, Y-, and Z-axes. The gradient magnetic fields generated along the X-, Y-, and Z-axes by the gradient coil 103 are, for example, a slice gradient magnetic field Gs, a phase-encoding gradient magnetic field Ge, and a read-out gradient magnetic field Gr. The gradient power supply 104 is configured to supply the electric current to the gradient coil 103.

The couch 105 includes a couchtop 105a on which the patient P is placed. Under control of the couch controlling circuitry 106, the couchtop 105a is inserted to the inside of the hollow space (an image taking opening) of the gradient coil 103 while the patient P is placed thereon. Normally, the couch 105 is installed in such a manner that the longitudinal direction thereof extends parallel to the central axis of the static magnetic field magnet 101. Under control of the image processing device 130, the couch controlling circuitry 106 is configured to drive the couch 105 so as to move the couchtop 105a in longitudinal directions and up-and-down directions.

The transmitter coil 107 is arranged on the inside of the gradient coil 103 and is configured to generate a radio frequency magnetic field by receiving supply of a Radio Frequency (RF) pulse from the transmitter circuitry 108. The transmitter circuitry 108 is configured to supply the transmitter coil 107 with the RF pulse corresponding to a Larmor frequency determined by the type of a target atom and the intensity of the magnetic field.

The receiver coil 109 is arranged on the inside of the gradient coil 103 and is configured to receive a magnetic resonance signal (which hereinafter may be referred to as "MR signal" as necessary) emitted from the patient P due to the influence of the radio frequency magnetic field. When having received the magnetic resonance signal, the receiver coil 109 is configured to output the received magnetic resonance signal to the receiver circuitry 110.

The transmitter coil 107 and the receiver coil 109 described above are merely examples. It is possible to use one or a combination of two or more, from among the following: a coil having only a transmitting function; a coil having only a receiving function; and a coil having transmitting and receiving functions.

The receiver circuitry 110 is configured to detect the magnetic resonance signal output from the receiver coil 109 and to generate magnetic resonance data based on the detected magnetic resonance signal. More specifically, the receiver circuitry 110 is configured to generate the magnetic resonance data by performing a digital conversion on the magnetic resonance signal output from the receiver coil 109. Further, the receiver circuitry 110 is configured to transmit the generated magnetic resonance data to the sequence controlling circuitry 120. Alternatively, the receiver circuitry 110 may be provided on the side of a gantry device including the static magnetic field magnet 101, the gradient coil 103, and the like.

The sequence controlling circuitry 120 is configured to perform an image taking process on the patient P, by driving the gradient power supply 104, the transmitter circuitry 108, and the receiver circuitry 110, based on sequence information transmitted thereto from the image processing device 130. In this situation, the sequence information is information defining a procedure for performing the image taking process. The sequence information defines: the intensity of the electric current to be supplied by the gradient power supply 104 to the gradient coil 103 and the timing with which the electric current is to be supplied; the intensity of the RF pulse to be supplied by the transmitter circuitry 108 to the transmitter coil 107 and the timing with which the RF pulse is to be applied; the timing with which the magnetic resonance signal is to be detected by the receiver circuitry 110, and the like. For example, the sequence controlling circuitry 120 may be an integrated circuit such as an Application Specific Integrated Circuit (ASIC) or a Field Programmable Gate Array (FPGA), or an electronic circuit such as a Central Processing Unit (CPU) or a Micro Processing Unit (MPU). Details of pulse sequences executed by the sequence controlling circuitry 120 will be explained later.

Further, when having received the magnetic resonance data from the receiver circuitry 110 as a result of performing the image taking process on the patient P by driving the gradient power supply 104, the transmitter circuitry 108, and the receiver circuitry 110, the sequence controlling circuitry 120 transfers the received magnetic resonance data to the image processing device 130.

The image processing device 130 is configured to exercise overall control of the magnetic resonance imaging apparatus 100, to generate images, and the like. The image processing device 130 includes a memory 132, an input device 134, a display 135, and processing circuitry 150. The processing circuitry 150 includes an interface function 131, a controlling function 133, and a generating function 136.

In the first embodiment, processing functions performed by the interface function 131, the controlling function 133, and the generating function 136 are stored in the memory 132 in the form of computer-executable programs. The processing circuitry 150 is a processor configured to realize the functions corresponding to the programs, by reading and executing the programs from the memory 132. In other words, the processing circuitry 150 that has read the programs has the functions illustrated within the processing circuitry 150 in FIG. 1. With reference to FIG. 1, the example is explained in which the single processing circuitry (i.e., the processing circuitry 150) realizes the processing functions implemented by the interface function 131, the controlling function 133, and the generating function 136; however, another arrangement is also acceptable in which the processing circuitry 150 is structured by combining together a plurality of independent processors, so that the functions are realized as a result of the processors executing the programs. In other words, each of the functions described above may be configured as a program, so that the single processing circuitry (i.e., the processing circuitry 150) executes the programs. In another example, one or more specific functions may be installed in a dedicated independent program-executing circuit. In FIG. 1, the interface function 131, the controlling function 133, and the generating function 136 are examples of a receiving unit, a controlling unit, a generating unit, and an analyzing unit, respectively. Further, the sequence controlling circuitry 120 is an example of the sequence controlling unit.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 132.

Alternatively, instead of saving the programs in the memory 132, it is also acceptable to directly incorporate the programs in the circuits of the one or more processors. In that situation, the one or more processors realize the functions by reading and executing the programs incorporated in the circuits thereof. Similarly, the couch controlling circuitry 106, the transmitter circuitry 108, the receiver circuitry 110, and the like are also structured by using one or more electronic circuits such as the processors described above.

By employing the interface function 131, the processing circuitry 150 is configured to transmit the sequence information to the sequence controlling circuitry 120 and to receive the magnetic resonance data from the sequence controlling circuitry 120. Further, when having received the magnetic resonance data, the processing circuitry 150 including the interface function 131 is configured to store the received magnetic resonance data into the memory 132.

The magnetic resonance data stored in the memory 132 is arranged into a k-space by the controlling function 133. As a result, the memory 132 stores k-space data therein.

The memory 132 is configured to store therein the magnetic resonance data received by the processing circuitry 150 including the interface function 131, the k-space data arranged in the k-space by the processing circuitry 150 including the controlling function 133, image data generated by the processing circuitry 150 including the generating function 136, and the like. For example, the memory 132 is a semiconductor memory element such as a Random Access Memory (RAM) or a flash memory, or a hard disk, an optical disk, or the like.

The input device 134 is configured to receive various types of instructions and inputs of information from an operator. For example, the input device 134 may be a pointing device such as a mouse or a trackball, may be a selecting device such as a mode changing switch, or may be an inputting device such as a keyboard. Under control of the processing circuitry 150 including the controlling function 133, the display 135 is configured to display a Graphical User Interface (GUI) used for receiving an input of an image taking condition, an image generated by the processing circuitry 150 including the generating function 136, and the like. The display 135 is, for example, a display monitor such as a liquid crystal display monitor.

By employing the controlling function 133, the processing circuitry 150 exercises overall control of the magnetic resonance imaging apparatus 100 and to control image taking processes, image generating processes, image display processes, and the like. For example, the processing circuitry 150 including the controlling function 133 is receives an input of the image taking condition (an image taking parameter or the like) through the GUI and to generate the sequence information according to the received image taking condition. Further, the processing circuitry 150 including the controlling function 133 is configured to transmit the generated sequence information to the sequence controlling circuitry 120.

By employing the generating function 136, the processing circuitry 150 is configured to generate an image by reading the k-space data from the memory 132 and performing a reconstruction process such as a Fourier transform on the read k-space data.

Next, the background of the embodiment will briefly be explained.

In magnetic resonance imaging, there is a method called three-dimensional ultrashort echo time (3D UTE) imaging method. The 3D UTE imaging method has the following characteristics: signals have high sensitivity because the echo time (TE) is short; resistance to motion artifact is relatively high because oversampling is performed at the center of a k-space; and the imaging is not easily affected by susceptibility.

To selectively capture an image of a blood vessel, it is desirable to suppress background signals (and fat signals). Accordingly, it is possible to render the aorta, the abdominal aorta, peripheral sites, and the like in images by applying a tag pulse while using a Time-Spatial Labeling Inversion Pulse (Time-SLIP) method and combining 3D UTE acquisition with a flow-in method of the Time-SLIP scheme. By combining the 3D UTE imaging with the Time-SLIP method in this manner, it is possible to acquire three-dimensional k-space data, while suppressing the background signals.

For blood vessels having a relatively high flow rate, it is possible to render the blood vessel in images by combining the 3D UTE acquisition with the Time-SLIP method; however, to render a blood vessel having a relatively low flow rate like in the situations where Non-Contrast Magnetic Resonance Angiography (NC-MRA) is implemented on a peripheral site, it is difficult to render the blood vessel in images by simply combining the 3D UTE acquisition with the Time-SLIP method.

To cope with these circumstances, the magnetic resonance imaging apparatus 100 according an embodiment executes, while a k-space is divided into a plurality of segments, a pulse sequence by which a tag pulse is applied, and subsequently, acquisition is performed by repeatedly performing the acquisition at the center of the k-space. In this situation, the sequence controlling circuitry 120 executes the pulse sequence while changing the range to which the tag pulse is applied (hereinafter, "tag pulse application range") for each of the plurality of segments.

With these arrangements, it is possible to effectively render the blood vessel in an image, even in a site or the like where the flow rate is low and it would be difficult to have the blood vessel rendered by using the conventional method.

The above configuration will be explained with reference to FIGS. 2A to 9.

Figure 2B:
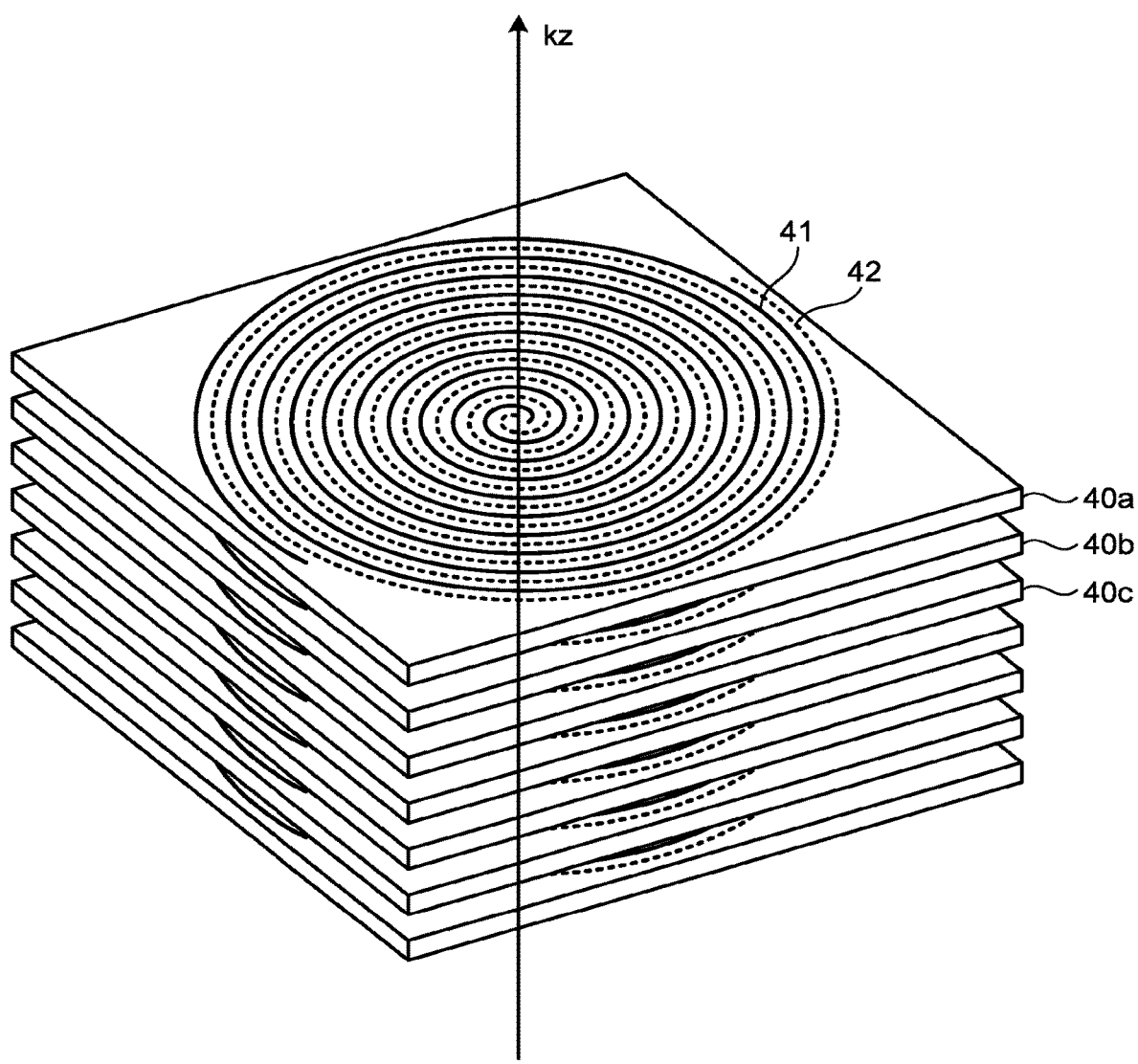
Figure 2C:
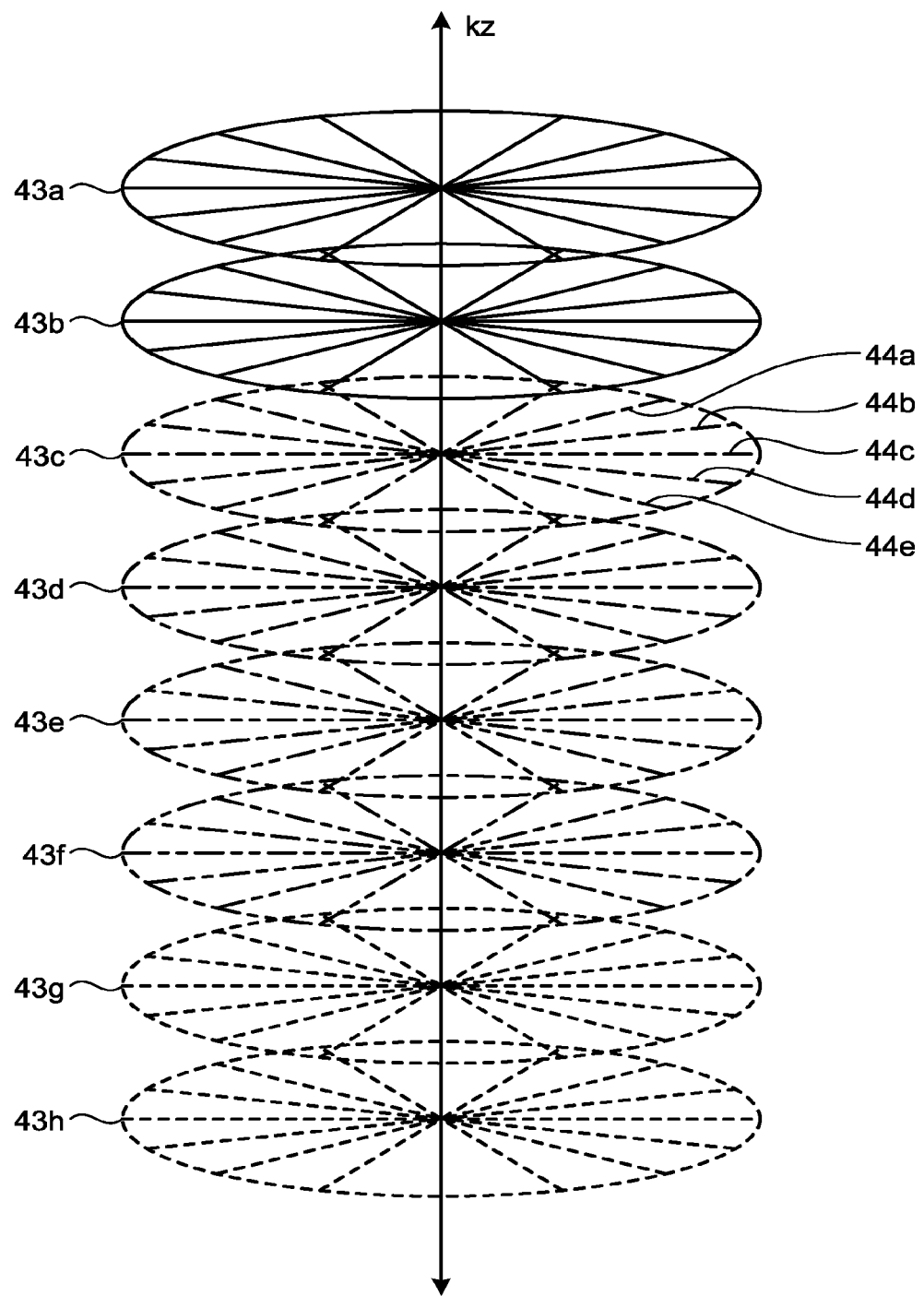

In the embodiment, the sequence controlling circuitry 120 is configured to execute the pulse sequence by which the acquisition is performed by repeatedly performing the acquisition at the center of the k-space. Examples of these acquisition processes in which the acquisition is repeatedly performed at the center of the k-space are illustrated in FIGS. 2A, 2B, and 2C. FIGS. 2A, 2B, and 2C are drawings illustrating the examples of the acquisition processes performed by the magnetic resonance imaging apparatus 100 according to the embodiment. More specifically, FIG. 2A illustrates an example of three-dimensional spherical acquisition, whereas FIG. 2B illustrates an example of spiral acquisition, and FIG. 2C illustrates an example of stack-of-star acquisition. When implementing the three-dimensional UTE imaging, the sequence controlling circuitry 120 performs the acquisition by using the three-dimensional spherical acquisition illustrated in FIG. 2A.

FIG. 2A illustrates the example of the three-dimensional spherical acquisition. When implementing the three-dimensional UTE acquisition, the sequence controlling circuitry 120 performs the three-dimensional spherical acquisition as illustrated in FIG. 2A, so as to perform a center-out acquisition where the acquisition is performed from the center of the k-space toward the outside. The lines 10a, 10b, and 10c each indicate the acquisition of one line. Further, the sequence controlling circuitry 120 may perform an additional acquisition process by performing a Cartesian sampling process on the central part of the k-space by using, for example, a Pointwise Encoding Time Reduction with Radial Acquisition (PETRA) sequence or the like.

FIG. 2B illustrates the example of the spiral acquisition. When performing the spiral acquisition, the sequence controlling circuitry 120 acquires three-dimensional k-space data by performing spiral acquisition on the inside of a two-dimensional plane and sequentially acquiring k-space data in positions different from the inside of the two-dimensional plane in terms of the perpendicular direction (k, direction). Planes 40*a*, 40*b*, and 40*c* indicate the two-dimensional stacks in that situation. On the inside of each of the two-dimensional planes, the sequence controlling circuitry 120 performs a center-out acquisition from the center of the k-space toward the outside, along either a spiral 41 or 42, for example.

FIG. 2C illustrates the example of the stack-of-star acquisition. When performing the stack-of-star acquisition, the sequence controlling circuitry 120 acquires three-dimensional k-space data by performing radial acquisition on the inside of a two-dimensional plane and sequentially acquiring k-space data in positions different from the inside of the two-dimensional plane in terms of the perpendicular direction (k, direction). Planes 43*a*, 43*b*, 43*c*, 43*d*, 43*e*, 43*f*, 43*g*, and 43*h* indicate the two-dimensional stacks in that situation. The sequence controlling circuitry 120 performs an out-center-out acquisition by which, within each of the two-dimensional planes, for example, the acquisition starts from the outside of the k-space, goes through the center of the k-space, and proceeds toward the outside of the k-space again, along each of the lines. Lines 44*a*, 44*b*, 44*c*, 44*d*, 44*e*, and so on indicate those lines.

In an embodiment, the sequence controlling circuitry 120 is configured to execute a pulse sequence by which the acquisition performed by repeatedly performing the acquisition at the center of the k-space such as that in the three-dimensional UTE imaging is combined with a method such as the Time-SLIP method by which background signals are suppressed by using the application of a tag pulse. An overall configuration of the pulse sequence executed by the sequence controlling circuitry 120 will be explained, with reference to FIG. 3A.

Figure 3A:
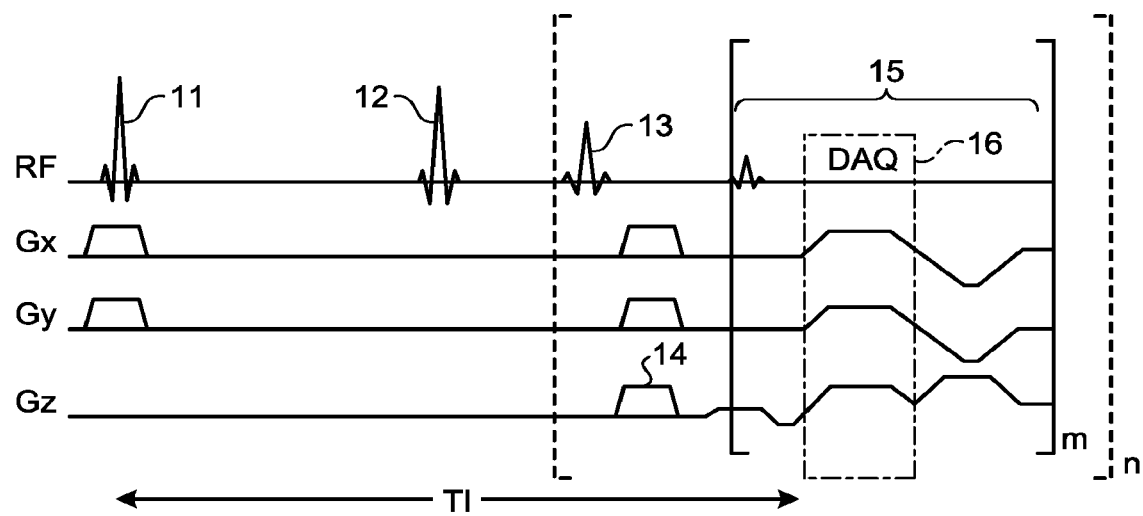
FIGS. 3A and 3B are drawings for explaining a pulse sequence executed by sequence controlling circuitry 120 according to the present embodiment.

At first, the sequence controlling circuitry 120 applies a tag pulse 11. In this situation, the sequence controlling circuitry 120 applies the tag pulse while changing the tag pulse application range, for each of plurality of segments. These processes will be explained later. Of the pulse sequence, FIG. 3A illustrates a part that is repeated per application of one tag pulse. Every time a tag pulse is applied, the same pulse sequence is repeatedly executed.

Subsequently, after the application of the tag pulse 11, the sequence controlling circuitry 120 applies a venous suppressing pulse 12, as necessary. After that, in a data acquisition time period 16, the sequence controlling circuitry 120 executes an acquisition sequence 15. In one example, in the data acquisition time period 16, the sequence controlling circuitry 120 executes a 3D UTE sequence, as the acquisition sequence 15. In one example, as the 3D UTE sequence, the sequence controlling circuitry 120 executes a pulse sequence that generates gradient echo, by applying a half pulse and subsequently applying a combination of predetermined gradient magnetic fields.

In FIG. 3A, m denotes a fat suppression loop in which after applying a fat suppression pulse 13 and a spoiler 14, the sequence controlling circuitry 120 repeats the acquisition sequence 15 with respect to mutually-different k-space segments as many times as m. Further, n denotes a tag loop. In other words, per tag pulse 11, the sequence controlling circuitry 120 executes the acquisition sequence 15 with respect to the mutually-different k-space segments of which the quantity is equal to n×m. The sequence controlling circuitry 120 executes these processes with respect to a plurality of tag pulses. In this manner, while the k-space is divided into the plurality of segments, the sequence controlling circuitry 120 executes the pulse sequence by which the tag pulse 11 is applied, and subsequently, the acquisition is performed by executing the acquisition sequence 15.

When the acquisition has been performed with respect to each of all the segments of the k-space while the position of the tag pulse is fixed, it is possible to obtain normal k-space data with respect to the tag pulse position.

Figure 3B:
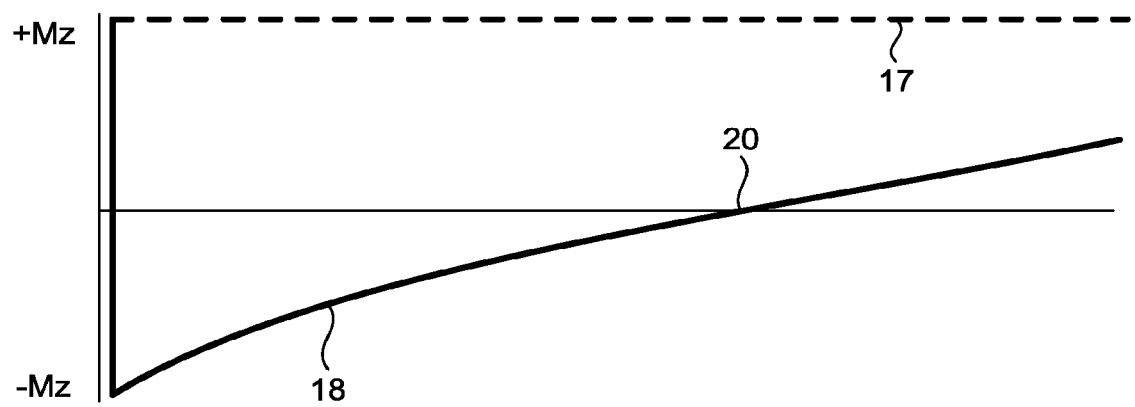

Next, an impact imposed on signal values by the application of the tag pulse will be explained, with reference to FIG. 3B. In FIG. 3B, a curve 17 indicates behaviors of longitudinal magnetization in regions other than the application region of the tag pulse 11. Another curve 18 indicates behaviors of longitudinal magnetization of a spin that was present in the application region of the tag pulse 11 at the time of the application of the tag pulse 11. As indicated by the curve 17, no change was observed in the longitudinal magnetization of the spin that was not present in the application region of the tag pulse 11 at the time of the application of the tag pulse 11. In contrast, as indicated by the curve 18, the longitudinal magnetization of the spin that was present in the application region of the tag pulse 11 was inverted by the tag pulse 11 and subsequently gradually became relaxed. When the sequence controlling circuitry 120 executes an acquisition sequence at a null point 20 at which the longitudinal magnetization becomes zero, it is possible to suppress the signal of the longitudinal magnetization of a spin that was present in the application region of the tag pulse 11 at the time of the application of the tag pulse 11 and was present in the imaged region at the time of the acquisition (the data acquisition time period 16). In this manner, because the contrast occurs between the spin to which the tag pulse was applied and the spin to which no tag pulse was applied, it is possible to make use of this contrast.

There is a variety of patterns of the tag pulse applied by the sequence controlling circuitry 120. For example, there are various methods such as a flow-in method by which only a region selecting tag pulse is applied; a flow-out method by which a region selecting tag pulse and a non-region-selecting pulse are applied; and a tag-on/tag-off method by which an image taking process is performed twice in total, namely, one time with application of a region selecting tag pulse and the other time without the application of the region selecting tag pulse, so as to perform a difference calculating process between the two.

FIG. 4 is a flowchart for explaining a process performed by the magnetic resonance imaging apparatus according to the first embodiment.

At first, at step S100, to execute a pulse sequence, the sequence controlling circuitry 120 applies the tag pulse, while changing the range to which the tag pulse 11 is applied for each of the plurality of segments.

In one example, while keeping constant the width of the region to which the tag pulse 11 is applied, the sequence controlling circuitry 120 executes a pulse sequence while changing the position in which the application of the tag pulse is started, for each of the plurality of segments.

Figure 5A:
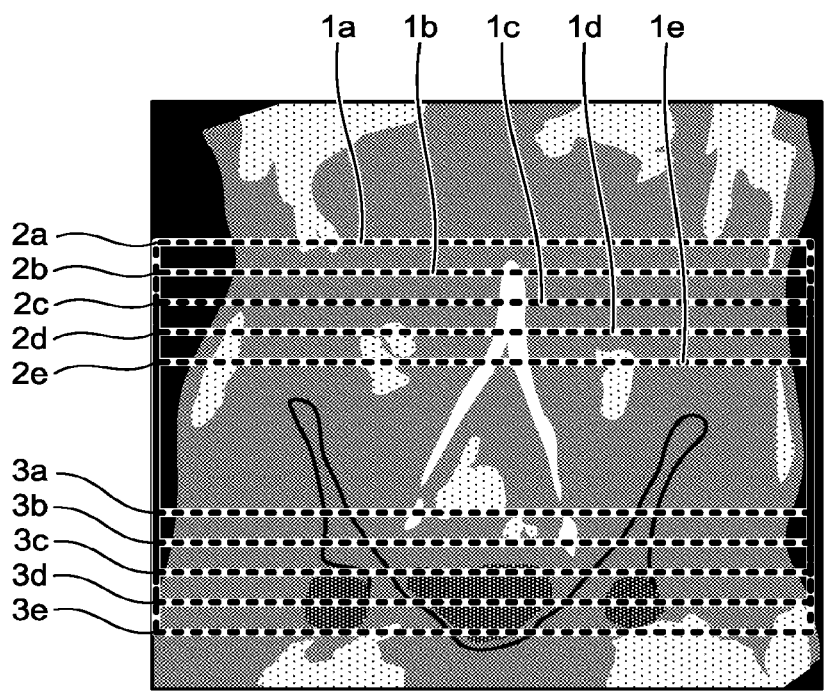
FIGS. 5A and 5B are drawings for explaining a process performed by the magnetic resonance imaging apparatus according to the first embodiment.

The above example is illustrated in FIG. 5A. The sequence controlling circuitry 120 applies: a first tag pulse to a region 1*a*, which is a rectangular region from a start position 2*a* to an end position 3*a*; a second tag pulse to a region 1*b*, which is a rectangular region from a start position 2*b* to an end position 3*b*; a third tag pulse to a region 1*c*, which is a rectangular region from a start position 2*c* to an end position 3*c*; a fourth tag pulse to a region 1*d*, which is a rectangular region from a start position 2*d* to an end position 3*d*; and a fifth tag pulse to a region 1*e*, which is a rectangular region from a start position 2*e* to an end position 3*e*. In this manner, the sequence controlling circuitry 120 applies the tag pulses, by translating (in a parallel movement) the application region of the tag pulse little by little, for each of the segments on which the acquisition is performed.

The reason why the sequence controlling circuitry 120 applies the tag pulses while changing the application region of the tag pulse for each of the plurality of segments can be explained as follows:

The tag pulse application range is usually moved after the acquisition of all of the k-space data has been performed. In other words, it is considered possible to obtain information related to a blood flow by repeatedly performing the operation of: applying a tag pulse to a certain region; acquiring the data related to all the segments in the k-space; and changing the application region of the tag pulse after having acquired the data related to all the segments in the k-space data. However, generally speaking, because three-dimensional acquisition takes a long imaging time period, if the tag pulse application region were changed after waiting until the data of all the segments in the k-space becomes available, it would be possible to sufficiently render the blood flow only when the blood flow is fast, which means that, when the blood flow is slow, it would not be possible to sufficiently render the blood flow. To cope with this situation, the magnetic resonance imaging apparatus 100 according to the present embodiment is configured to change the region to which the tag pulse is applied for each of the plurality of segments. As a result, it is possible to achieve a sufficient in-flow effect on moving fluid such as an artery, a vein, Cerebrospinal Fluid (CSF), or pancreatic secretion, for example, even when the target subject to the image taking process moves slowly.

If the pulse sequence executed by the sequence controlling circuitry 120 were, for example, a pulse sequence by which k-space data is acquired by implementing a Cartesian sampling method, when the tag pulse application region is changed for each of the plurality of segments, it is expected that errors might increase. However, in the present embodiment, because the pulse sequence executed by the sequence controlling circuitry 120 is a pulse sequence of such a type by which the acquisition is repeatedly performed at the center of the k-space, the errors do not easily increase, which justifies performing the process described above.

Returning to the description of FIG. 4, at step S110, the sequence controlling circuitry 120 applies a venous suppression pulse 12.

Subsequently, at step S120, the sequence controlling circuitry 120 applies the fat suppression pulse 13, and subsequently executes the acquisition sequence 15, which is a 3D UTE imaging sequence, for example, so as to acquire the k-space data during the data acquisition time period 16 including the null point 20. In the present example with the pulse sequence illustrated in FIG. 3A, because m denotes the fat suppression loop, whereas n denotes the tag loop, every time the fat suppression pulse 13 is applied, the acquisition sequence 15 is repeated as many times as m. Also, every time the tag pulse 11 is applied, the application of the fat suppression pulse 13 and the following fat suppression loop are repeated as many times as n. Further, in the example illustrated in FIG. 5A, the number of tag divisions is "5" so that application of five tag pulses forms one set. Accordingly, a plurality of sets are further repeated with respect to different k-spaces.

Figure 5B:
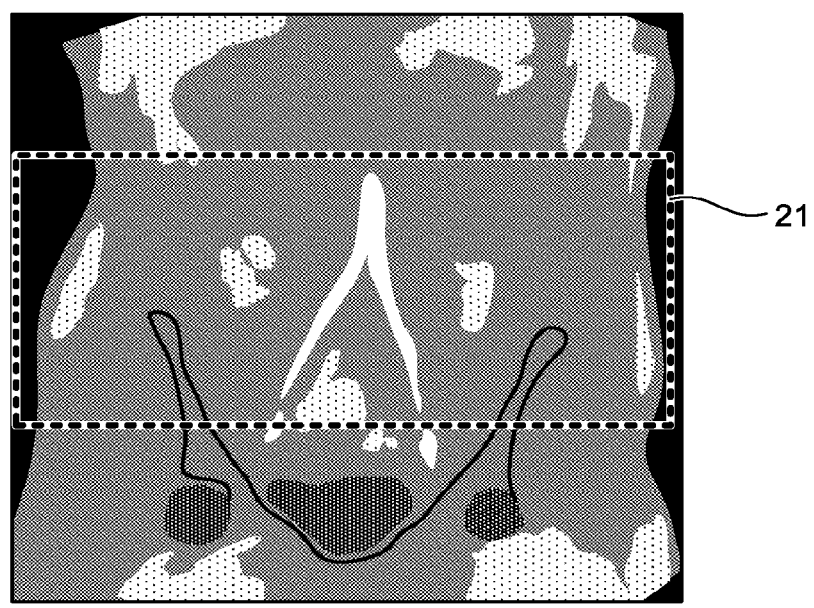
Figure 6:
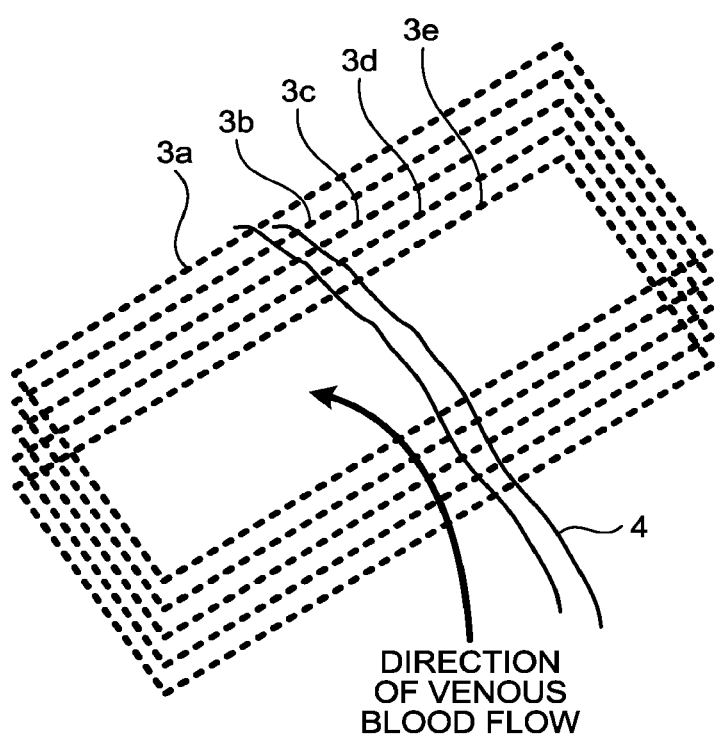
FIG. 6 is a drawing for explaining regions to which a tag pulse is applied in the first embodiment.

When the application regions of the tag pulse 11 are the regions illustrated in FIG. 5A, an imaging region 21 in FIG. 5B is a typical imaging region.

Subsequently, at step S130, by employing the generating function 136, the processing circuitry 150 generates a magnetic resonance image based on the pulse sequence executed by the sequence controlling circuitry 120 at steps S100 through S120.

In this situation, at step S100, when the sequence controlling circuitry 120 executes the pulse sequence while changing the application range of the tag pulse 11 in a direction parallel to the direction in which the blood vessel extends, it is possible to efficiently render the flow of the blood in images. For example, when the extending direction of a blood vessel 4 is such as that illustrated in FIG. 6, it is desirable to configure the sequence controlling circuitry 120 to change the application range of the tag pulse 11 from the region 3a, to 3b, 3c, 3d, and 3e.

Figure 7A:
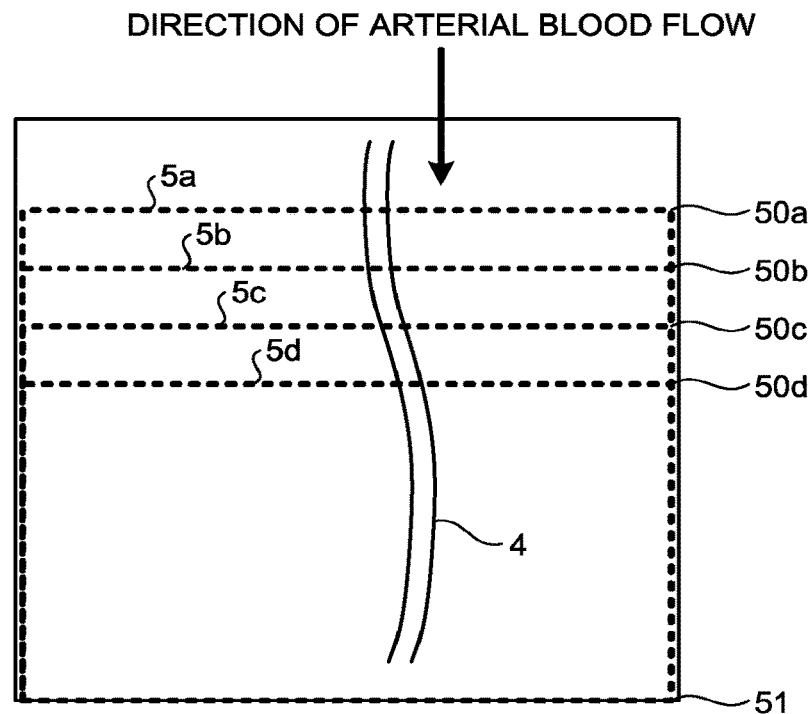
FIGS. 7A and 7B are more drawings for explaining regions to which a tag pulse is applied in the first embodiment.
Figure 7B:
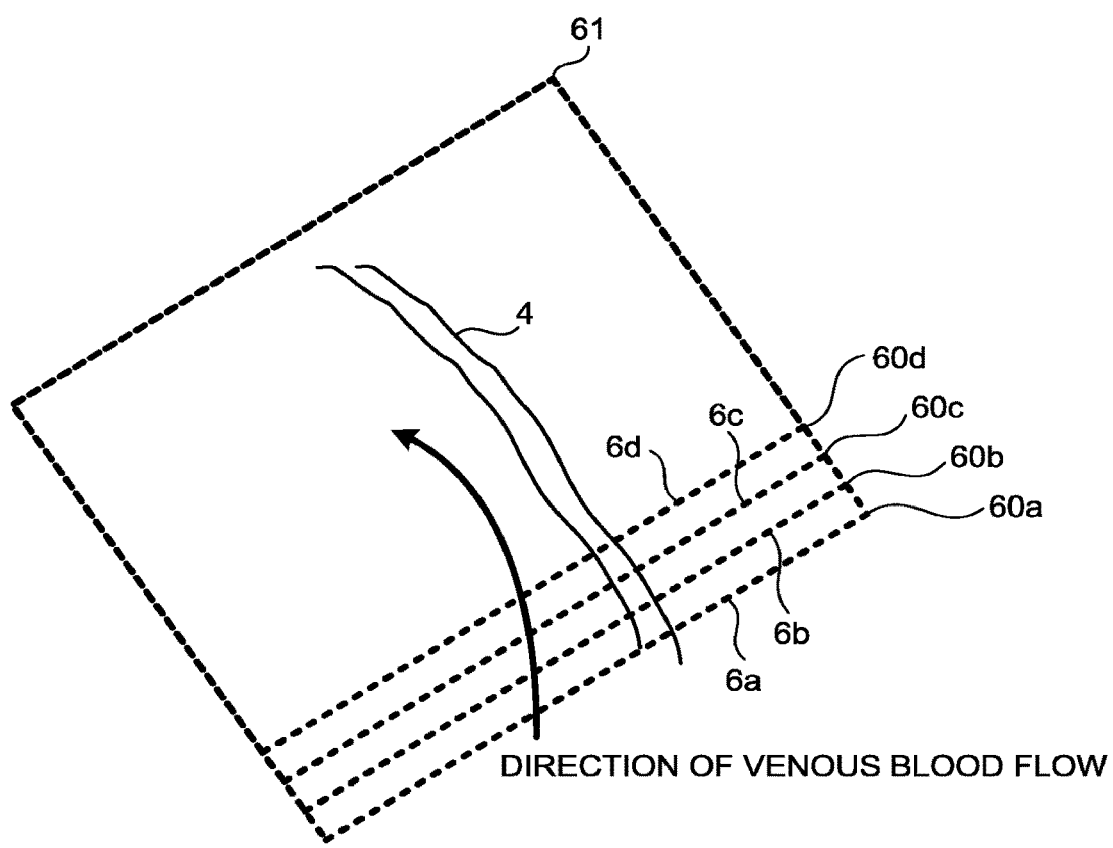

Further, at step S100, in another example among various methods for changing the tag pulse application region, the sequence controlling circuitry 120 may execute a pulse sequence while changing the width of the application region of the tag pulse 11 for each of the plurality of segments, while keeping constant the position in which the application of the tag pulse 11 is ended (or started). For example, as illustrated in FIG. 7A, the sequence controlling circuitry 120 may execute a pulse sequence while narrowing the width of the application region of the tag pulse 11 for each of the plurality of segments, by applying: a first tag pulse 5a using a position 50a as the start position of the tag pulse 11; a second tag pulse 5b using a position 50b as the start position of the tag pulse 11; a third tag pulse 5c using a position 50c as the start position of the tag pulse 11; and a fourth tag pulse 5d using a position 50d as the start position of the tag pulse 11, while keeping constant the position 51 in which the application of the tag pulse 11 is ended. By changing the tag pulse application region in this manner, the eventual image quality may be stabilized because the position in which the application of the tag pulse 11 is ended is fixed.

Further, also when the method described above is used for changing the tag pulse application region, it is also acceptable to optimize the direction in which the tag pulse application region is changed with respect to the direction in which the blood vessel extends, when the extending direction of the blood vessel is diagonal. For example, when the extending direction of the blood vessel 4 is such as that illustrated in FIG. 7B, the sequence controlling circuitry 120 may execute a pulse sequence while changing the application range of the tag pulse 11 in a direction parallel to the extending direction of the blood vessel. For example, the sequence controlling circuitry 120 executes a pulse sequence by narrowing the width of the application region of the tag pulse 11 for each of the plurality of segments, by applying: a first tag pulse 6a using a position 60a as the start position of the tag pulse 11; a second tag pulse 6b using a position 60b as the start position of the tag pulse 11; a third tag pulse 6c using a position 60c as the start position of the tag pulse 11; and a fourth tag pulse 6d using a position 60d as the start position of the tag pulse 11, while keeping constant the position 61 in which the application of the tag pulse 11 is ended.

Further, in an adaptive example, the sequence controlling circuitry 120 may simultaneously apply tag pulses to a plurality of regions. Further, the sequence controlling circuitry 120 may change the region to which the tag pulse 11 is applied, by using mutually-different changing methods among the plurality of regions.

Figure 8A:
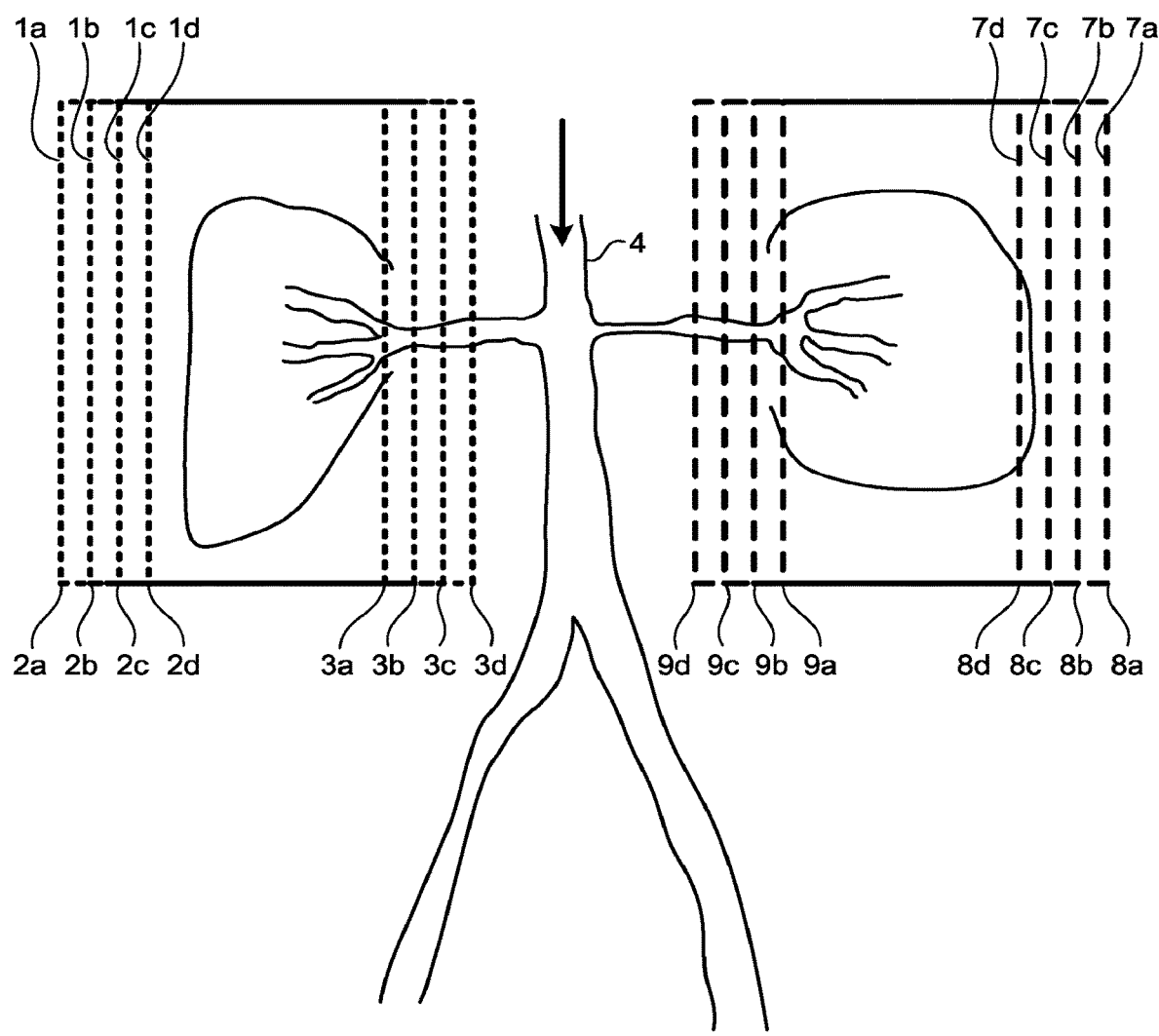
FIGS. 8A and 8B are other drawings for explaining regions to which a tag pulse is applied in the first embodiment.

In one example, as illustrated in FIG. 8A, the sequence controlling circuitry 120 applies: the first tag pulse to a region 1a, which is the region from a start position 2a to an end position 3a, and to a region 7a, which is the region from a start position 8a to an end position 9a; a second tag pulse to a region 1b, which is the region from a start position 2b to an end position 3b, and to a region 7b, which is the region from a start position 8b to an end position 9b; a third tag pulse to a region 1c, which is the region from a start position 2c to an end position 3c, and to a region 7c, which is the region from a start position 8c to an end position 9c; and a fourth tag pulse to a region 1d, which is the region from a start position 2d to an end position 3d, and to a region 7d, which is the region from a start position 8d to an end position 9d. In this situation, the sequence controlling circuitry 120 varies the width by which the tag pulse start position changes, for each of the plurality of regions to which the tag pulses are simultaneously applied. With this arrangement, the sequence controlling circuitry 120 is able to optimize the image taking process to suit the imaged subject.

Figure 8B:
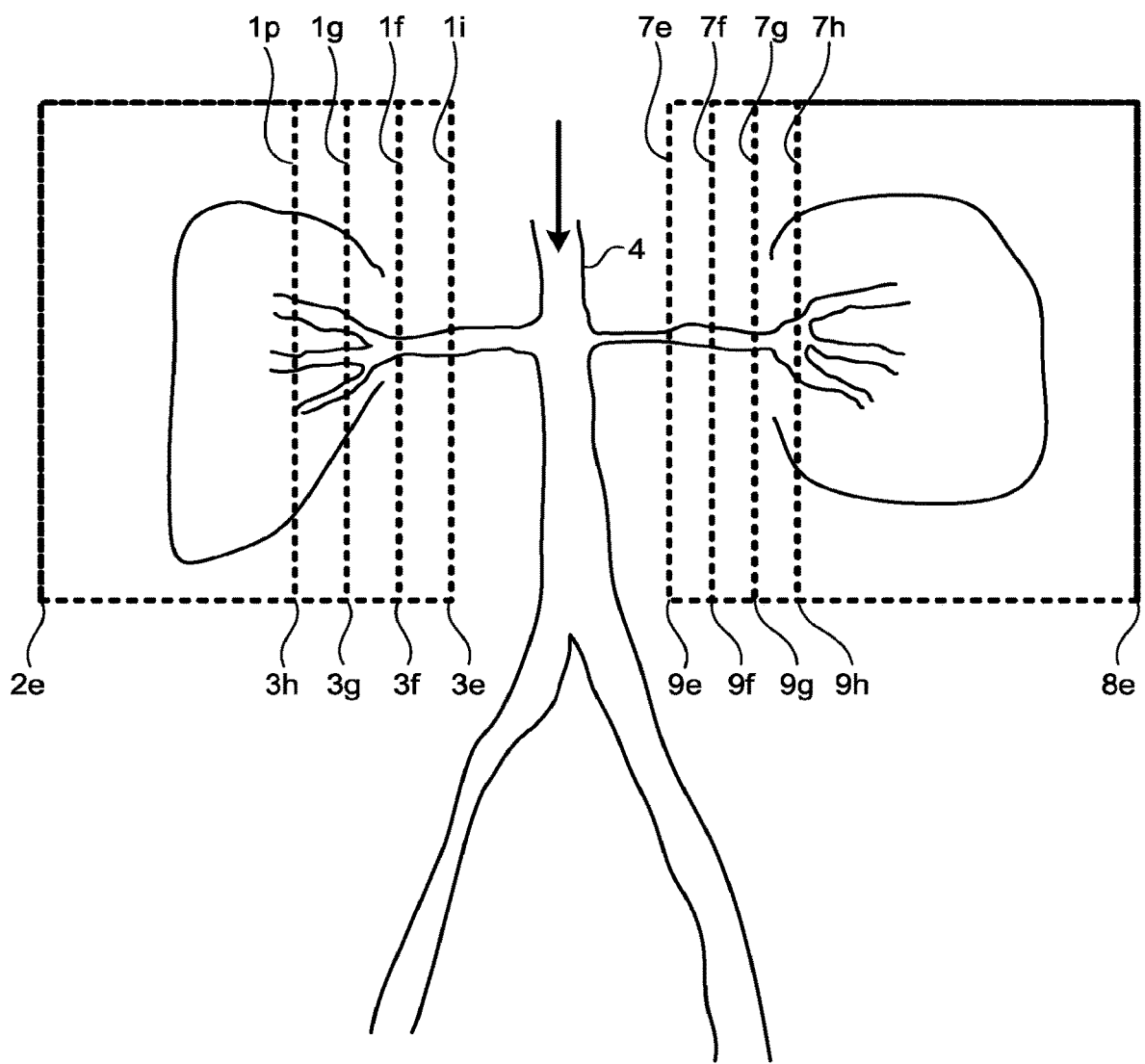

Similarly, as illustrated in FIG. 8B, it is also acceptable to execute a pulse sequence by changing the width of the application region of the tag pulse 11 for each of the plurality of segments by applying: a plurality of tag pulses as first tag pulses 1i and 7e while using positions 3e and 9e as the start positions of the tag pulse 11; a plurality of tag pulses as second tag pulses if and 7f while using positions 3f and 9f as the start positions of the tag pulse 11; a plurality of tag pulses as third tag pulses 1g and 7g while using positions 3g and 9g as the start positions of the tag pulse 11; and a plurality of tag pulses as fourth tag pulses 1p and 7h while using positions 3h and 9h as the start positions of the tag pulse 11, while keeping constant the positions 2e and 8e in which the application of the tag pulse 11 is ended.

Figure 9:
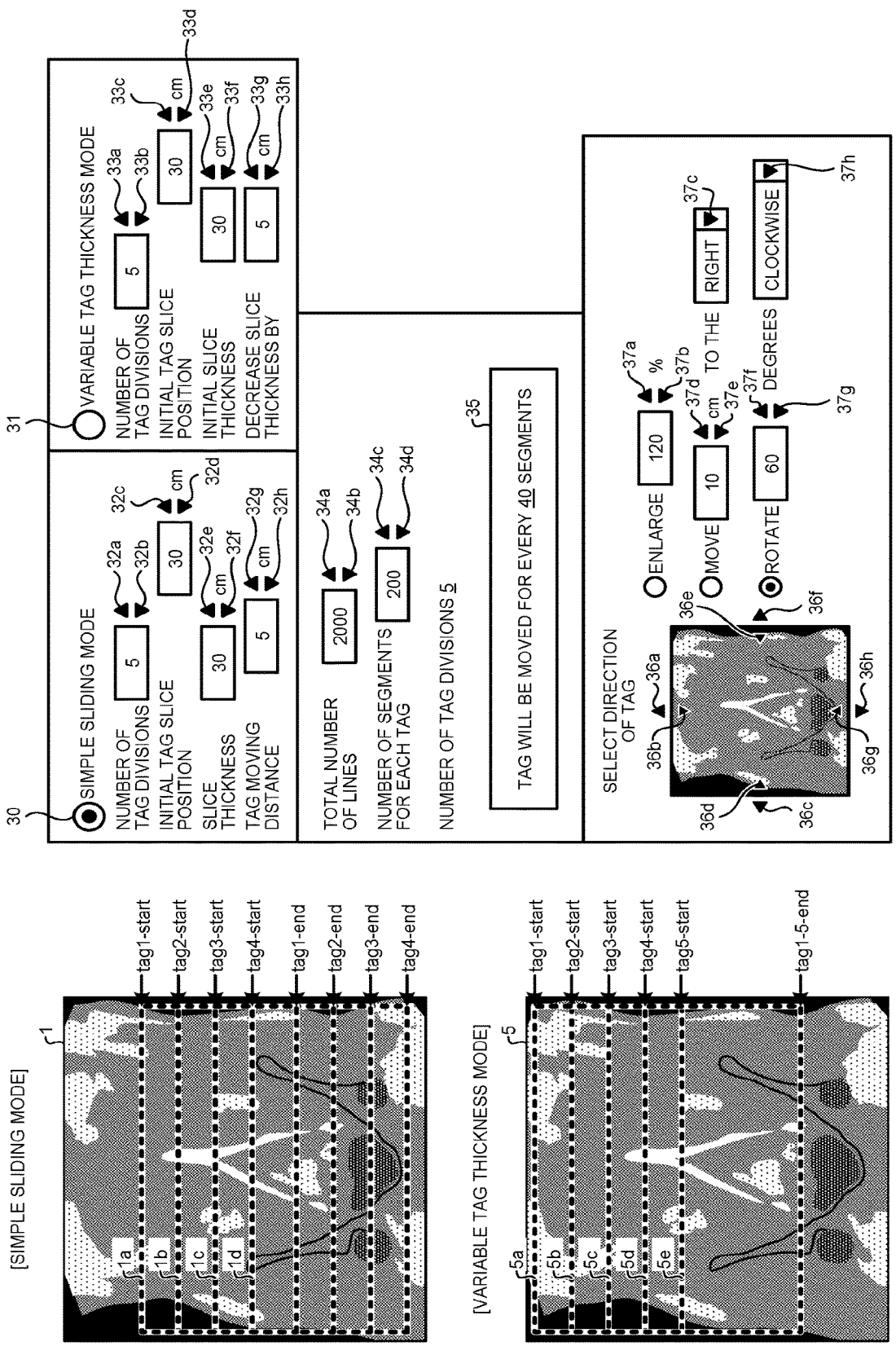
FIG. 9 is a drawing for explaining an example of Graphical User Interface (GUI) related to the magnetic resonance imaging apparatus according to the first embodiment.

FIG. 9 illustrates an example of a Graphical User Interface (GUI).

By employing the controlling function 133, the processing circuitry 150 is configured to receive, via the input device 134 configured to receive inputs from a user and via buttons 30 and 31, a selection of a mode for the application of the tag pulse 11 from between: a simple sliding mode in which the position in which the application of the tag pulse is started is changed for each of the segments, while keeping constant the width of the application region of the tag pulse 11; and a variable slice thickness mode in which the width of the application region of the tag pulse 11 is changed for each of the segments, while keeping constant the position in which the application of the tag pulse 11 is ended.

When the user clicks on the button 30 to select the simple sliding mode, the processing circuitry 150 receives, by employing the controlling function 133 and via the input device, a change in the number of tag divisions made by using buttons 32a and 32b; a change in an initial tag slice position made by using buttons 32c and 32d; a change in the slice thickness made by using buttons 32e and 32f; and a change in a tag moving distance for each of the tags made by using buttons 32g and 32h. The processing circuitry 150 further establishes settings of the tag pulses based on the received settings and causes the display 135 to display setting results in a display region 1. For example, when the number of tag divisions is "5", the initial tag slice position is at "30 cm", the slice thickness is "30 cm", and the tag moving distance is "5 cm", the sequence controlling circuitry 120 applies the first tag pulses to the positions of "0 cm to 30 cm", the second tag pulses to the positions of "−5 cm to 25 cm", the third tag pulses to the position of "−10 cm to 20 cm", the fourth tag pulses to the positions of "−15 cm to 15 cm"; and the fifth tag pulses to the positions of "−20 cm to 10 cm".

Further, when the user clicks on the button 31 to select the variable slice thickness mode, the processing circuitry 150 receives, by employing the controlling function 133 and via the input device, a change in the number of tag divisions made by using buttons 33a and 33b, a change in the initial tag slice position made by using buttons 33c and 33d, a change in the slice thickness made by using buttons 33e and 33f, and a change in the decreasing width for the slick thickness made by using buttons 33g and 33h. The processing circuitry 150 further establishes settings of the tag pulses based on the received settings and causes the display device 135 to display setting results in a display region 5. For example, when the number of tag divisions is "5", the initial tag slice position is at "30 cm", the initial slice thickness is "30 cm", and the slice thickness decrease is "3 cm", the sequence controlling circuitry 120 applies the first tag pulses to the positions of "0 cm to 30 cm", the second tag pulses to the positions of "0 cm to 27 cm", the third tag pulses to the position of "0 cm to 24 cm", the fourth tag pulses to the positions of "0 cm to 21 cm"; and the fifth tag pulses to the positions of "0 cm to 18 cm".

Further, by employing the controlling function 133 and via the input device 134, the processing circuitry 150 receives a change in the number of lines for the entire image taking process that is made by using buttons 34a and 34b; and a change in the number of segments (or lines) on which an image taking process is performed with a whole set of tag pulses that is made by using buttons 34c and 34d. Further, by employing the controlling function 133, the processing circuitry 150 calculates the number of segments (or lines) related to an image taking process with one tag pulse based on the number of segments on which an image taking process is performed with a whole set of tag pulses and the number of tag divisions and further causes the calculation result to be displayed in a display region 35. For example, when the number of segments on which an image taking process is performed with a whole set of tag pulses is 200, while the number of tag divisions is 5, the number of segments related to the image taking process with one tag pulse is calculated as 200/5=40.

Further, by employing the controlling function 133 and via the input device 134, the processing circuitry 150 is capable of receiving a change in the tag pulse application region. For example, by employing the controlling function 133 and via the input device 134, the processing circuitry 150 is capable of receiving: a change in the tag pulse application region made by using buttons 36a, 36b, 36c, 36d, 36e, 36f, 36g, 36g, 37c, 37d, and 37e; an enlargement/reduction of the tag pulse application region made by using buttons 37a and 37b; and a setting for a tag pulse application direction (an operation to rotate the tag pulse application region) made by using buttons 37f, 37g, and 37h.

By using the GUI configured in this manner, the sequence controlling circuitry 120 is capable of executing the pulse sequence while changing the application range of the tag pulse 11 for each of the plurality of segments, based on the inputs received from the user by the input device 134.

Computer Programs

It is possible to execute the instructions in the processing procedures described in any of the above embodiments, based on a computer program (hereinafter, "program") realized with software. As a result of a generic computer storing the program therein in advance and reading the program, it is also possible to achieve the same advantageous effects as those achieved by the magnetic resonance imaging apparatus 100 according to the above embodiments. The instructions described in any of the above embodiments may be recorded in a magnetic disk (e.g., a flexible disk, a hard disk), an optical disk (e.g., a Compact Disk Read-Only Memory [CD-ROM], a Compact Disk Recordable [CD-R], a Compact Disk Rewritable [CD-RW], a Digital Versatile Disk Read-Only Memory [DVD-ROM], DVD±Recordable [DVD±R], DVD±Rewritable [DVD±RW]), a semiconductor memory, or a similar recording medium, as a computer-executable program. As long as the storage medium is readable by a computer or an embedded system, it is possible to use any storage format. By reading the program from the recording medium and causing a CPU to execute the instructions written in the program based on the program, the computer is able to realize the same operations as those performed by the magnetic resonance imaging apparatus 100 according to any of the above embodiments. Further, when obtaining or reading the program, the computer may obtain or read the program via a network.

Further, based on the instructions of the program installed from the storage medium into the computer or the embedded system, an Operating System (OS) working in the computer or middleware (MW) such as database management software of a network may execute a part of the processes performed for realizing the embodiments described above. Further, the storage medium does not necessarily have to be a medium independent of the computer or the embedded system. Examples of the storage medium include a storage medium that downloads the program transferred via a Local Area Network (LAN) or the internet and that stores or temporarily stores therein the transferred program. Further, the number of storage media does not necessarily have to be one. Examples of the storage medium according to the embodiments include the situation where the processes according to the embodiments are executed from two or more media. It is possible to use any configuration for the medium (media).

The computer or the embedded system according to any of the embodiments is configured to execute the processes in the embodiment based on the program stored in the one or more storage media and may be configured as a single apparatus such as a personal computer or a microcomputer or as a system in which a plurality of apparatuses are connected together via a network. Further, the "computer" according to the embodiments does not necessarily have to be a personal computer and may be an arithmetic processing device included in an information processing device or a microcomputer. The term "computer" is a generic name for any device or apparatus capable of realizing the functions of the embodiments by using the program.

By using the magnetic resonance imaging apparatus according to at least one aspect of the embodiments described above, it is possible to effectively render fluid such as blood in the images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising:
sequence controlling circuitry configured, while a k-space is divided into a plurality of segments, to execute a pulse sequence by which a tag pulse is applied and subsequently acquisition is performed; and
processing circuitry configured to generate an image based on the pulse sequence executed by the sequence controlling circuitry,
wherein the pulse sequence is a pulse sequence by which the acquisition is repeatedly performed at a center of the k-space,
wherein the sequence controlling circuitry executes the pulse sequence, while changing a range to which the tag pulse is applied, for each of the plurality of segments, and
wherein the sequence controlling circuitry executes the pulse sequence while changing a position in which the application of the tag pulse is started for each of the plurality of segments, while keeping constant a width of a region to which the tag pulse is applied.

2. The magnetic resonance imaging apparatus according to claim 1, further comprising: an input device configured to receive an input from a user, wherein
based on the input received from the user by the input device, the sequence controlling circuitry executes the pulse sequence while changing the range to which the tag pulse is applied for each of the plurality of segments.

3. A magnetic resonance imaging apparatus comprising:
sequence controlling circuitry configured, while a k-space is divided into a plurality of segments, to execute a pulse sequence by which a tag pulse is applied and subsequently acquisition is performed; and
processing circuitry configured to generate an image based on the pulse sequence executed by the sequence controlling circuitry,
wherein the pulse sequence is a pulse sequence by which the acquisition is repeatedly performed at a center of the k-space,
wherein the sequence controlling circuitry executes the pulse sequence, while changing a range to which the tag pulse is applied, for each of the plurality of segments, and
wherein the sequence controlling circuitry executes the pulse sequence while changing a width of a region to which the tag pulse is applied for each of the plurality of segments, while keeping constant a position in which the application of the tag pulse is ended.

4. A magnetic resonance imaging apparatus comprising:
sequence controlling circuitry configured, while a k-space is divided into a plurality of segments, to execute a pulse sequence by which a tag pulse is applied and subsequently acquisition is performed; and
processing circuitry configured to generate an image based on the pulse sequence executed by the sequence controlling circuitry,
wherein the pulse sequence is a pulse sequence by which the acquisition is repeatedly performed at a center of the k-space,
wherein the sequence controlling circuitry executes the pulse sequence, while changing a range to which the tag pulse is applied, for each of the plurality of segments, and
wherein the sequence controlling circuitry performs three-dimensional ultrashort TE (3D UTE) acquisition, as the acquisition.

5. A magnetic resonance imaging apparatus comprising:
sequence controlling circuitry configured, while a k-space is divided into a plurality of segments, to execute a pulse sequence by which a tag pulse is applied and subsequently acquisition is performed; and
processing circuitry configured to generate an image based on the pulse sequence executed by the sequence controlling circuitry,
wherein the pulse sequence is a pulse sequence by which the acquisition is repeatedly performed at a center of the k-space,
wherein the sequence controlling circuitry executes the pulse sequence, while changing a range to which the tag pulse is applied, for each of the plurality of segments, and
wherein the sequence controlling circuitry performs one of spiral acquisition and Stack Of Stars acquisition.

6. A magnetic resonance imaging apparatus comprising:
sequence controlling circuitry configured, while a k-space is divided into a plurality of segments, to execute a pulse sequence by which a tag pulse is applied and subsequently acquisition is performed; and
processing circuitry configured to generate an image based on the pulse sequence executed by the sequence controlling circuitry,
wherein the pulse sequence is a pulse sequence by which the acquisition is repeatedly performed at a center of the k-space,
wherein the sequence controlling circuitry executes the pulse sequence, while changing a range to which the tag pulse is applied, for each of the plurality of segments, and
wherein the sequence controlling circuitry executes the pulse sequence while changing the range to which the tag pulse is applied, in a direction parallel to a direction in which a blood vessel extends.

7. A magnetic resonance imaging apparatus comprising:
sequence controlling circuitry configured, while a k-space is divided into a plurality of segments, to execute a pulse sequence by which a tag pulse is applied and subsequently acquisition is performed; and
processing circuitry configured to generate an image based on the pulse sequence executed by the sequence controlling circuitry,
wherein the pulse sequence is a pulse sequence by which the acquisition is repeatedly performed at a center of the k-space, and
wherein the sequence controlling circuitry executes the pulse sequence, while changing a range to which the tag pulse is applied, for each of the plurality of segments,
wherein the sequence controlling circuitry is configured to apply the tag pulse to a plurality of regions simultaneously, and
wherein the sequence controlling circuitry changes the region to which the tag pulse is applied, by using mutually-different changing methods among the plurality of regions.

8. A magnetic resonance imaging method implemented by a magnetic resonance imaging apparatus, the magnetic resonance imaging method comprising:
while a k-space is divided into a plurality of segments, executing a pulse sequence by which a tag pulse is applied and subsequently acquisition is performed; and
generating an image based on the pulse sequence,
wherein the pulse sequence is a pulse sequence by which the acquisition is repeatedly performed at a center of the k-space,
wherein the pulse sequence is executed while a range to which the tag pulse is applied is changed for each of the plurality of segments, and
wherein the pulse sequence is executed while changing a position in which the application of the tag pulse is started for each of the plurality of segments, while keeping constant a width of a region to which the tag pulse is applied.

* * * * *